(12) United States Patent
Lee

(10) Patent No.: US 9,005,159 B2
(45) Date of Patent: Apr. 14, 2015

(54) LIQUID INFUSION APPARATUS

(75) Inventor: Young Gyu Lee, Seoul (KR)

(73) Assignee: Woo Young Medical Co., Ltd., Chungcheongb uk-do (KR)

( * ) Notice: Subject to any disclaimer, the term of this patent is extended or adjusted under 35 U.S.C. 154(b) by 170 days.

(21) Appl. No.: 13/637,493

(22) PCT Filed: Mar. 31, 2011

(86) PCT No.: PCT/KR2011/002242
§ 371 (c)(1),
(2), (4) Date: Dec. 11, 2012

(87) PCT Pub. No.: WO2011/122886
PCT Pub. Date: Oct. 6, 2011

(65) Prior Publication Data
US 2013/0211323 A1    Aug. 15, 2013

(30) Foreign Application Priority Data

Apr. 1, 2010 (KR) .......... 10-2010-0030145
May 6, 2010 (KR) .......... 10-2010-0042493
May 6, 2010 (KR) .......... 10-2010-0042513

(51) Int. Cl.
| A61M 31/00 | (2006.01) |
| A61M 5/168 | (2006.01) |
| A61M 5/142 | (2006.01) |
| F04B 43/08 | (2006.01) |
| A61M 39/28 | (2006.01) |

(52) U.S. Cl.
CPC ....... *A61M 5/16854* (2013.01); *A61M 5/14228* (2013.01); *A61M 39/281* (2013.01); *A61M 2005/16863* (2013.01); *F04B 43/082* (2013.01); *A61M 5/14212* (2013.01)

(58) Field of Classification Search
USPC ..................... 604/65, 67, 131, 151
See application file for complete search history.

(56) References Cited

U.S. PATENT DOCUMENTS

| 4,373,525 | A | * | 2/1983 | Kobayashi | ............. 417/63 |
| 4,690,673 | A | * | 9/1987 | Bloomquist | ........... 604/67 |
| 5,098,380 | A | | 3/1992 | Aizawa et al. | |
| 6,572,604 | B1 | | 6/2003 | Platt et al. | |
| 7,255,683 | B2 | * | 8/2007 | Vanderveen et al. | ....... 604/118 |
| 8,382,447 | B2 | * | 2/2013 | Wang et al. | ............. 417/53 |

FOREIGN PATENT DOCUMENTS

| CN | 2764411 Y | 3/2006 |
| JP | 3106374 A | 5/1991 |
| JP | 11137683 A | 5/1999 |
| KR | 1019970006087 B1 | 4/1997 |
| KR | 1020020063001 A | 7/2002 |
| KR | 1020070019383 A | 2/2007 |

* cited by examiner

*Primary Examiner* — Aarti B Berdichevsky
(74) *Attorney, Agent, or Firm* — The Webb Law Firm

(57) ABSTRACT

The present invention relates to a liquid infusion apparatus, including: a finger module provided in a main body such that the finger module can elastically move backward from a liquid delivery tube; a tube clamp, in which two clamp bodies spaced apart from each other approach each other by means of restoring force of an elastic member upon the opening of a door during infusion, so as to compress and block the liquid delivery tube; and a tube blockage detection device which detects whether the liquid delivery tube is blocked by a cause, for example, when the outlet-side portion of the liquid delivery tube, which delivers medicinal liquid pumped by a liquid pump during infusion, is bent.

4 Claims, 13 Drawing Sheets

Fig.12
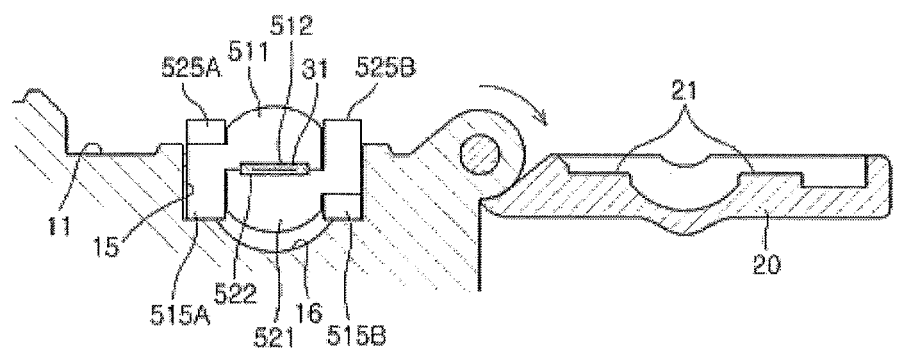
(A)
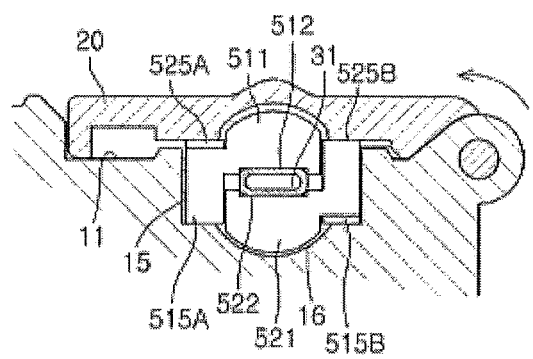
(B)

LIQUID INFUSION APPARATUS

TECHNICAL FIELD

The present invention relates to a liquid infusion apparatus which is used for infusion of medical liquid.

BACKGROUND ART

Generally, a liquid infusion apparatus which is used to infuse a medical liquid to a target such as a patient includes a main body, a door, a flexible liquid infusion tube, and a wiggling liquid infusion pump. FIG. 1 is a sectional view illustrating a portion of the typical liquid infusion apparatus. As shown in FIG. 1, the door 2 is openably provided on the main body 1. The liquid infusion tube 3 is disposed such that when the door 2 is closed, it is interposed between the main body 1 and the door 2. The liquid infusion pump includes fingers 4 which are arranged in parallel to each other, and a finger drive means (not shown) which move fingers 4 in a wiggling manner. When the door 2 that is openably provided on the main body 1 is in the closed state, the liquid infusion pump faces the door 2 so that the fingers 4 can compress a portion of the liquid infusion tube 3 interposed between the main body 1 and the door 2. Furthermore, a compressing member 5 is provided on the door 2 such that when the door 2 is closed, the compressing member 5 compresses a portion of the liquid infusion tube 3 interposed between it and the fingers 4. A plurality of coil springs 6 are provided between the compressing member 5 and the door 2 so that the compressing member 5 can elastically compress the liquid infusion tube 3. Although it is not shown in the drawings, a medical liquid injection unit such as an injection needle or catheter is connected to an end of the liquid infusion tube 3.

After the door 2 is closed and the liquid infusion tube 3 is interposed between the main body 1 and the door 2, the finger drive means is operated. Then, the fingers 4 repeatedly successively compress the portion of the liquid infusion tube 3 in the longitudinal direction. The compressing member 5 supports the liquid infusion tube 3 at a position opposing to the fingers 4 that are moving in the above-mentioned manner. Thus, medical liquid supplied from a medical liquid storage means to the liquid infusion tube 3 is transferred in constant amounts along the liquid infusion tube 3 by the compressing operation of the fingers 4 and the supporting function of the door 2. The medical liquid is infused into the target by the medical liquid injection unit. During this process, if an excessive load is applied to the liquid infusion tube 3 by the fingers 4, the compressing member 5 moves away from the liquid infusion tube 3 and supports the liquid infusion tube 3, thus preventing the liquid infusion tube 3 from being damaged.

However, in the conventional liquid infusion apparatus, the compressing member 5 and the coil spring 6 which are used to elastically compress the liquid infusion tube 3 are installed on the door 2. The structure of the door 2 is therefore complex. Further, when the door 2 opens, the complex structure of the door 2 is exposed to the outside, increasing the possibility of the door 2 being damaged. Hence, there is a disadvantage in that a separate element is required to cover the complex structure of the door 2 and protect it. Also the thickness of the door 2 is increased, making it difficult to modify the design of it to compactify the apparatus.

Moreover, if the door 2 opens when the conventional liquid infusion apparatus is being operated, transferring medical liquid from the liquid infusion pump cannot be controlled. In this case, medical liquid supplied from the medical liquid storage means to the liquid infusion tube 3 is directly infused into the target. Depending on the kind of medical liquid, the patient that is the target may be put into a coma or die of shock. Therefore, improvements are required to overcome the above problems.

Furthermore, when the conventional liquid infusion apparatus is being operated, if a portion of the liquid infusion tube 3 that is at an outlet-side based on the liquid infusion pump is undesirably bent or the medical liquid injection unit is filled with medical liquid, the liquid infusion tube 3 may be blocked. If the blocked liquid infusion tube 3 is neglected, infusion of medical liquid is interrupted, and the internal pressure of the liquid infusion tube 3 is increased by medical liquid which is continuously supplied by the liquid infusion pump, thus excessively expanding the liquid infusion tube 3 and damaging it. Thus, a device which can reliably detect whether the liquid infusion tube 3 is blocked during the liquid infusion process is required.

DISCLOSURE

Technical Problem

Accordingly, the present invention has been made keeping in mind the above problems occurring in the prior art, and an object of the present invention is to provide a liquid infusion apparatus which includes a means for compressing a liquid infusion tube that can simply and compactify the structure of a door. Another object of the present invention is to provide a liquid infusion apparatus which is configured such that the liquid infusion tube is blocked when the door opens. A further object of the present invention is to provide a liquid infusion apparatus which can reliably detect whether the liquid infusion tube has been blocked during a liquid infusion process.

Technical Solution

In order to accomplish the above objects, in an aspect, the present invention provides a liquid infusion apparatus, including: a main body having an opening; a door installed on the main body so as to be openable, wherein when the door is closed, the door faces the opening with a liquid infusion tube interposed between the door and the opening and supports the liquid infusion tube; a finger module comprising a plurality of fingers installed in the main body so as to be movable forward and backward relative to the opening, the fingers moving in conjunction with a cam shaft in a wiggling manner in which the fingers successively move forward to the opening and compress a portion of the liquid infusion tube through the opening; an elastic member applying elastic force to the finger module and biasing the finger module forward so that the liquid infusion tube is elastically compressed by the fingers; and cam shaft drive means rotating the cam shaft so that the fingers move in conjunction with the cam shaft in the wiggling manner.

The finger module may include a mounting block provided such that the fingers are able to move in conjunction with the cam shaft in the wiggling manner and compress the liquid infusion tube, wherein the mounting block may be mounted to the main body in such a way that the mounting block is able to move forward and backward relative to the opening under guidance of a guide, and the cam shaft drive means may include a motor and a power transmission unit transmitting rotational force of the motor to the cam shaft, wherein the motor may be installed in the mounting block, and the cam shaft drive means may move along with the finger module forward and backward relative to the opening.

The mounting block may have a shaft support part supporting an output shaft of the motor, and the motor may be coupled to the shaft support part by a coupling member made of an anti-vibration material.

The main body may include a front casing having the opening; and a rear casing coupled to the front casing. The guide may include a plurality of guide pins coupled to the front casing and disposed in predetermined portions of the mounting block. The elastic member may comprise a plurality of elastic members provided around the respective guide pins to bias the mounting block forward.

Furthermore, a shock absorber may be provided on at least one of portions of the main body and the finger module that face each other.

The liquid infusion apparatus may further include a cover sheet covering the opening to prevent a foreign substance from entering the main body through the opening, the cover sheet being made of a soft material.

In another aspect, the present invention provides a liquid infusion apparatus, including: a door installed on a main body so as to be openable, wherein when the door is closed, the door faces the main body with a liquid infusion tube interposed between the door and the main body and supports the liquid infusion tube; a finger module comprising a plurality of fingers moving in conjunction with a cam in a wiggling manner, the fingers facing the door with the liquid infusion tube interposed between the door and the fingers, the finger module being mounted to the main body by elastic means such that the finger module is able to successively compress a portion of the liquid infusion tube using the fingers that move in the wiggling manner and be elastically retracted from the liquid infusion tube; and drive means for operating the cam so that the fingers move in conjunction with the cam in the wiggling manner.

In a further aspect, the present invention provides a liquid infusion apparatus including: a main body in which a wiggling liquid infusion pump is installed, the liquid infusion pump compressing a liquid infusion tube to conduct liquid infusion; a door installed on the main body so as to be openable, wherein when the door is closed, the door faces the liquid infusion pump with a liquid infusion tube interposed between the door and the liquid infusion pump and supports the liquid infusion tube that is compressed by the liquid infusion pump; a tube clamp blocking the liquid infusion tube when the door opens and releasing the liquid infusion tube that has been blocked when the door is closed, wherein the clamp includes: a first clamp body disposed between the main body and the door that is closed, and facing the main body with the liquid infusion tube interposed between the tube clamp and the main body; a second clamp body facing the first clamp body with the liquid infusion tube interposed between the first clamp body and the second clamp body; and an elastic member applying elastic force to the first and second clamp bodies so that the first and second clamp bodies move toward each other and compress the liquid infusion tube, wherein the first clamp body includes a leg protruding toward the second clamp body and coming into contact with the main body, and the second clamp body comprises a leg protruding toward the first clamp body so that when the door is closed, the leg of the second clamp body comes into contact with the door whereby the second clamp body moves away from the first clamp body, and the main body has a space-forming depression in a predetermined portion facing the second clamp body, the space-forming depression defining a space in which the second clamp body can move away from the first clamp body. Here, at least one leg may be provided on each of opposite sides of the first and second clamp bodies.

The legs of the first and second clamp bodies may make a pair and contact each other while being disposed at a first side of the opposite sides of the first and second clamp bodies, and the legs of the first and second clamp bodies may also make a pair and contact each other while being disposed at a second side of the opposite sides of the first and second clamp bodies, so that movement of the first and second clamp bodies that move toward or away from each other is guided by the legs.

The legs that make a pair at the first side and the legs that make a pair at the other side may be arranged such that the legs alternate with each other.

The first and second clamp bodies may respectively have protrusions provided on each of the opposite sides of the first and second clamp bodies, the protrusions making a pair and forming a band holder, and the elastic member may comprise elastic members fitted over the respective band holders so that the first and second clamp bodies are biased to each other by the band holders. The band holder may have an expanded width on an end thereof to prevent the clamp band from being removed therefrom.

The tube clamp may further include a guide guiding the first and second clamp bodies that are moving toward or away from each other.

In a yet another aspect, the present invention provides a liquid infusion apparatus, including: a main body provided with a liquid infusion pump conducting a wiggling motion that successively compresses a portion of a flexible liquid infusion tube for transferring a medical liquid; a door installed on the main body so as to be openable, wherein when the door is closed, the door faces the liquid infusion pump with a liquid infusion tube interposed between the door and the liquid infusion pump and supports the liquid infusion tube that is compressed by the liquid infusion pump; a movable member facing the closed door with a portion of an outlet-side of the liquid infusion tube interposed between the movable member and the door and provided for transferring the medical liquid, the movable member installed in the main body so as to be movable forward and backward with respect to the portion of the outlet-side of the liquid infusion tube so that when the movable member moves forward, the movable member approaches the portion of the outlet-side of the liquid infusion tube; an elastic member applying elastic force to the movable member and biasing the movable member forward so that the movable member can approach the portion of the outlet-side of the liquid infusion tube; displacement detecting means detecting whether the movable member has been moved backward by expansion of the portion of the outlet-side of the liquid infusion tube which is caused by congestion of the medical liquid transferred by the liquid infusion pump; and a control unit determining whether the liquid infusion tube has been blocked depending on a result of the detection of the displacement detecting means.

The liquid infusion apparatus may further include indication means for indicating whether the liquid infusion tube is blocked or not under the control of the control unit.

The liquid infusion apparatus may further include a mounting housing in which the movable member is provided so as to be reciprocatable, with a through hole formed in the mounting housing at a position that faces one of opposite ends of the movable member with respect to a direction in which the movable member moves, wherein the movable member may have a protruding part that protrudes out of the mounting housing through the through hole, the main body may have a control hole formed at a position facing the portion of the outlet-side of the liquid infusion tube, the control hole being used to move the movable member backward, and the mounting housing may be installed in the main body such that the through hole is aligned with the control hole, wherein the movable member may move forward or backward relative to the portion of the outlet-side of the liquid infusion tube through the through hole aligned with the control hole.

The liquid infusion apparatus may further include a cover sheet made of a soft material and provided between the main body and the mounting housing to cover the control hole.

The cover sheet may cover the mounting housing such that the through hole is closed, thus covering the control hole between the main body and the mounting housing. The cover sheet may have water resistance.

The liquid infusion apparatus may further include a guide guiding movement of the movable member provided in the mounting housing.

The displacement detecting means may include: a magnet mounted to the movable member, the magnet moving along with the movable member; and a magnetic force measurement sensor disposed at a position spaced apart from the magnet by a predetermined distance in the direction in which the movable member moves, the magnetic force measurement sensor measuring magnetic force of the magnet. The control unit may compare a measured value input from the magnetic force measurement sensor with a preset value, thus determining whether the liquid infusion tube has been blocked.

Advantageous Effects

According to the present invention, a liquid infusion pump is installed in a main body such that it can elastically compress a liquid infusion tube. This can solve the problems of the conventional technique, such as the complex structure of the door and the increased volume of the door, which result from the construction in which elements for preventing excessive pressure from damaging the liquid infusion tube are provided on the door. Furthermore, in the present invention, even if the door opens during the liquid infusion process, the tube clamp compresses the liquid infusion tube and closes it, thus preventing an incorrect liquid infusion amount, for example, infusion of an excessive amount of medical liquid into a target such as a patient. In addition, during the liquid infusion process, a tube-blockage detecting device can detect whether an outlet-side portion of the liquid infusion tube that is transferring medical liquid from the liquid infusion pump is blocked or not. Therefore, the present invention can reliably cope with the problem of the liquid infusion tube being blocked.

DESCRIPTION OF DRAWINGS

FIGS. 5 through 7 illustrate the construction and installation structure of a liquid infusion pump of FIGS. 3 and 4, wherein FIG. 5 is an exploded perspective view, FIG. 6 is a plan view, and FIG. 7 is a front view from the direction of the arrow B of FIG. 3;

FIG. 12 shows sectional views illustrating the installation structure and operation of the tube clamp;

FIGS. 13 through 15 are views illustrating a tube-blockage detecting device of the liquid infusion pump according to the present invention, wherein FIG. 13 is a perspective view, FIG. 14 is an exploded perspective view, and FIG. 15 is a block diagram;

BEST MODE

Hereinafter, a preferred embodiment of the present invention will be described in detail with reference to the attached drawings.

Figure 1:
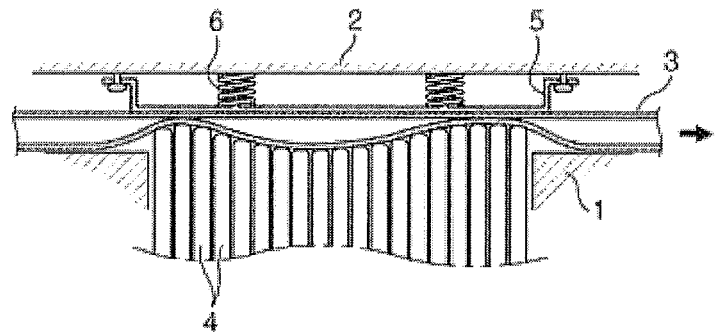
FIG. 1 is a sectional view showing a portion of a typical liquid infusion apparatus.
Figure 2:
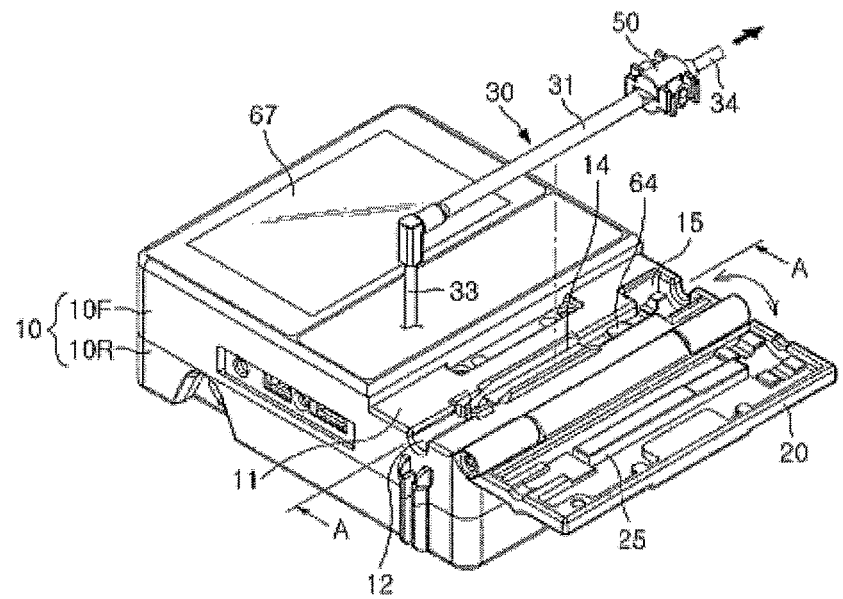
FIGS. 2 and 3 are perspective views illustrating a liquid infusion apparatus, according to the present invention.
Figure 3:
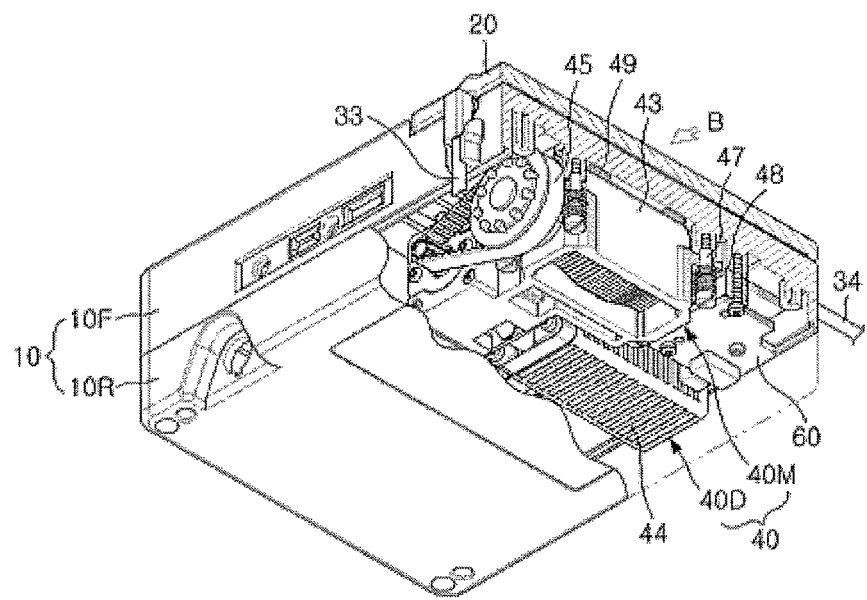

FIGS. 2 and 3 are perspective views illustrating a liquid infusion apparatus, according to the present invention. As shown in the drawings, the liquid infusion apparatus according to the present invention includes a main body 10, a door 20, a liquid infusion tube 30, and a wiggling liquid infusion pump 40. The door 20 covers a portion of the main body 10. The liquid infusion tube 30 is partially interposed between the door 20 and the main body 10. The liquid infusion tube 30 transfers medical liquid supplied from a medical liquid storage means (not shown). A medical liquid injection unit (not shown) such as an injection needle or catheter is connected to an end of the liquid infusion tube 30. The liquid infusion pump 40 compresses, successively with respect to the longitudinal direction, the portion of the liquid infusion tube 30 that is interposed between the main body 10 and the door 20, so that a fixed quantity of medical liquid that is supplied from the medical liquid storage means to the liquid infusion tube 30 can be transferred.

The main body 10 includes a front casing 10F and a rear casing 10R which is coupled to the front casing 10F. A covered surface 11 which is covered with the door 20 is formed on one end of a front surface of the front casing 10F. The door 20 is coupled to the end of the front casing 10F so as to be vertically rotatable so that, depending on a direction in which the door 20 rotates, it is opened or closed. When the door 20 is closed, the door 20 faces the covered surface 11 and covers it. Although it is not shown in the drawings, the closed state of the door 20 is maintained by a locking device.

Figure 4:
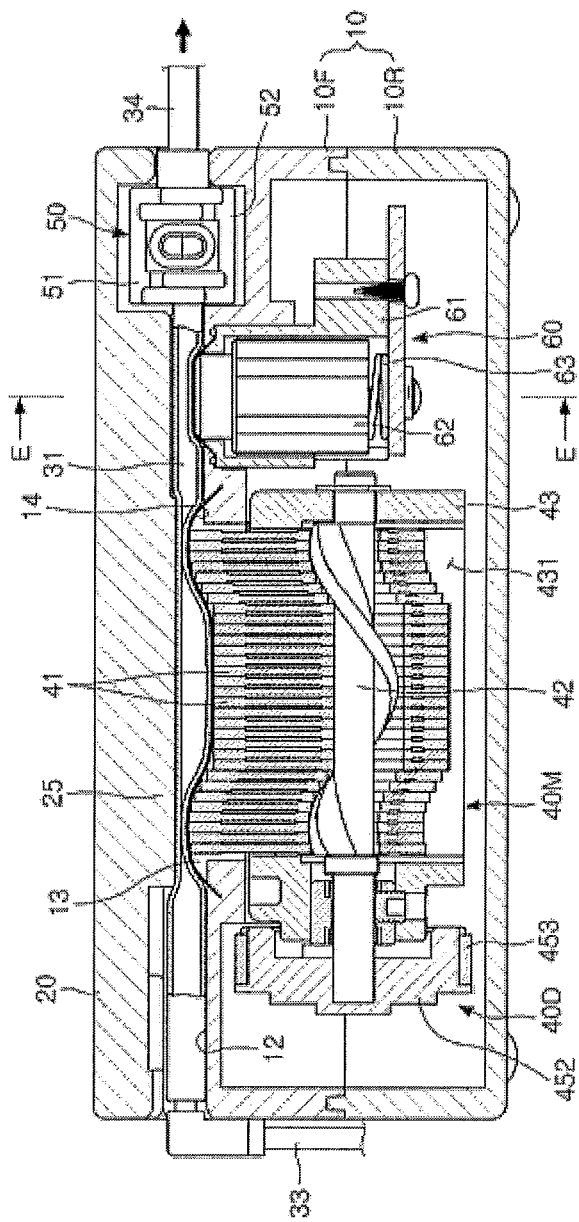
FIG. 4 is a sectional view taken along line A-A of FIG. 2.

FIG. 4 is a sectional view taken along line A-A of FIG. 2. As shown in FIG. 4, a tube seating depression 12 is linearly formed in the covered surface 11 in a left-right direction. A portion of the liquid infusion tube 30 is seated into the tube seating depression 12. The entirety of the liquid infusion tube 30 or the portion thereof that is seated into the tube seating depression 12 is flexible. In this embodiment, the portion of the liquid infusion tube 30 that is seated into the tube seating depression 12 is formed of a silicon tube 31. PVC tubes 33 and 34 are respectively connected to opposite ends of the silicon tube 31 by tube connectors. The door 20 is provided with a compressing member 25 which compresses the silicon tube 31 that has been seated in the tube seating depression 12, when the door 20 is closed. Although it is not shown in the drawings, an elastic member may be interposed between the door 20 and the compressing member 25.

A finger hole 13 which is an opening is formed in a central portion of a bottom of the tube seating depression 12. The finger hole 13 is closed by a cover sheet 14 which is made of a soft material, so that foreign substances can be prevented from entering the main body 10 through finger hole 13. Preferably, the finger hole cover sheet 14 has water resistance and functions as a waterproofing sheet.

Figure 5:
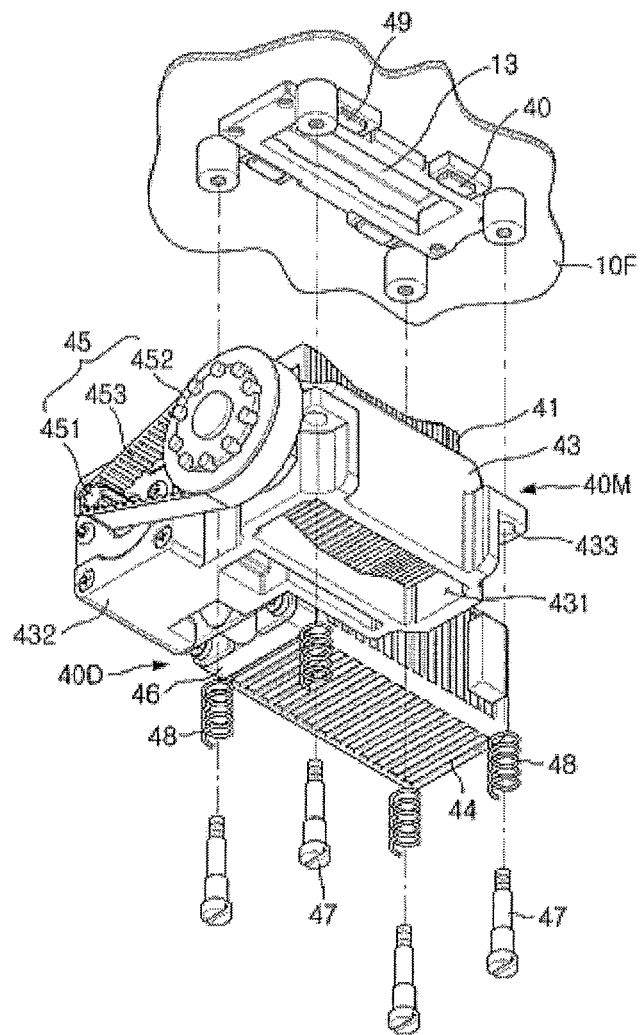
Figure 6:
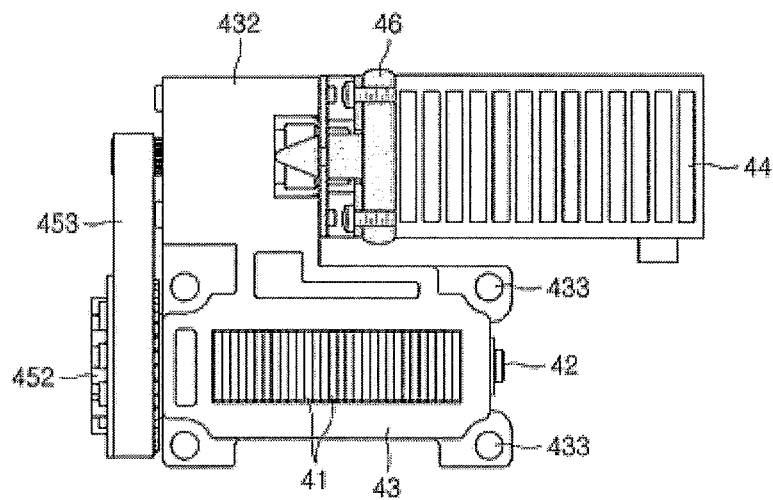
Figure 7:
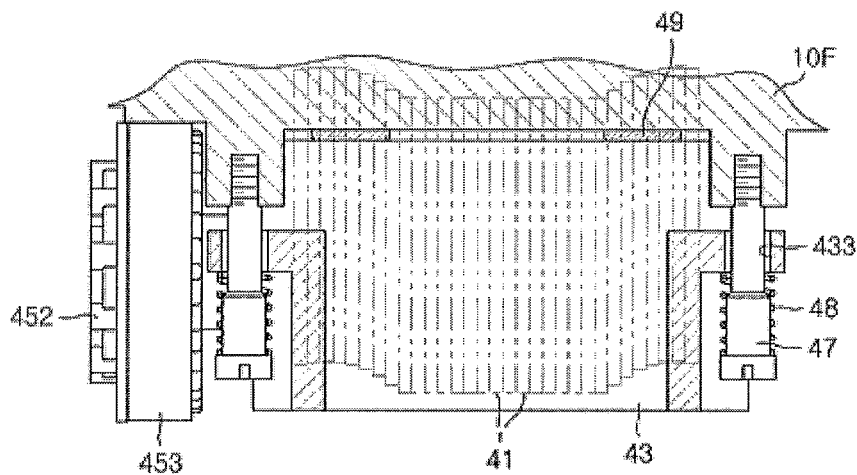
Figure 8:
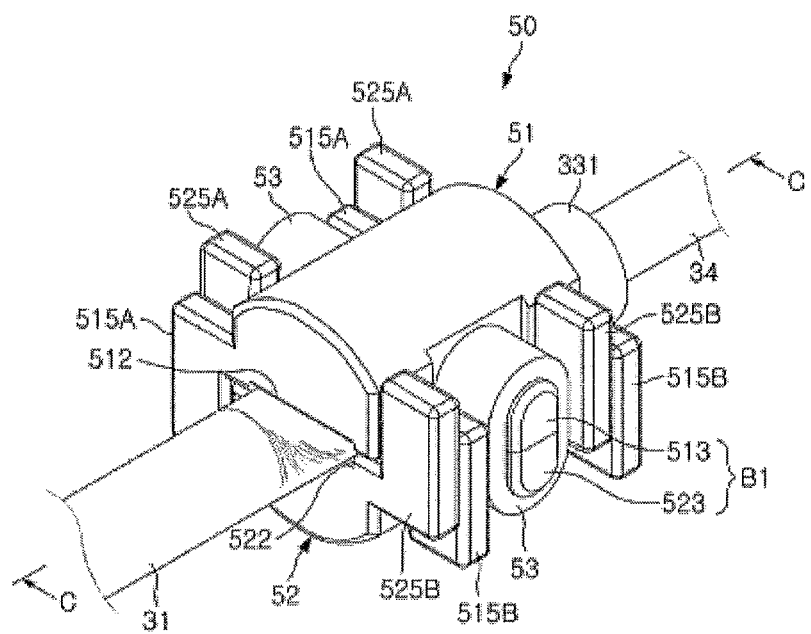
FIGS. 8 and 9 are respectively a perspective view and an exploded perspective view showing a tube clamp of the liquid infusion apparatus according to the present invention.
Figure 9:
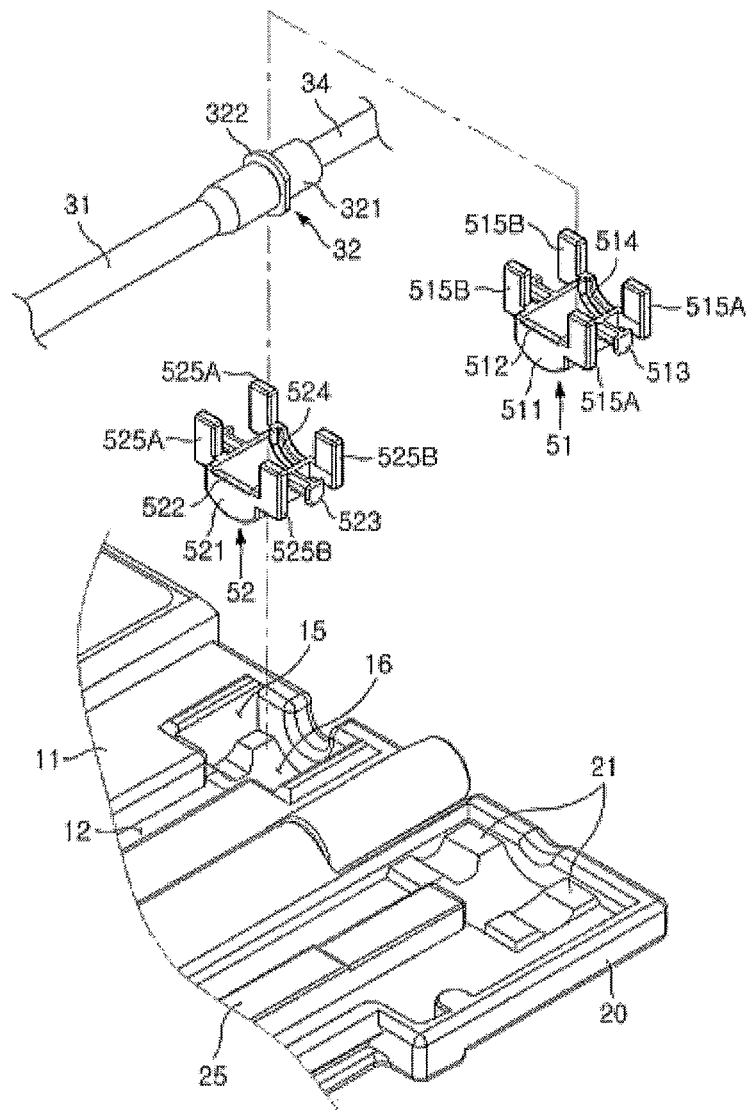
Figure 10:
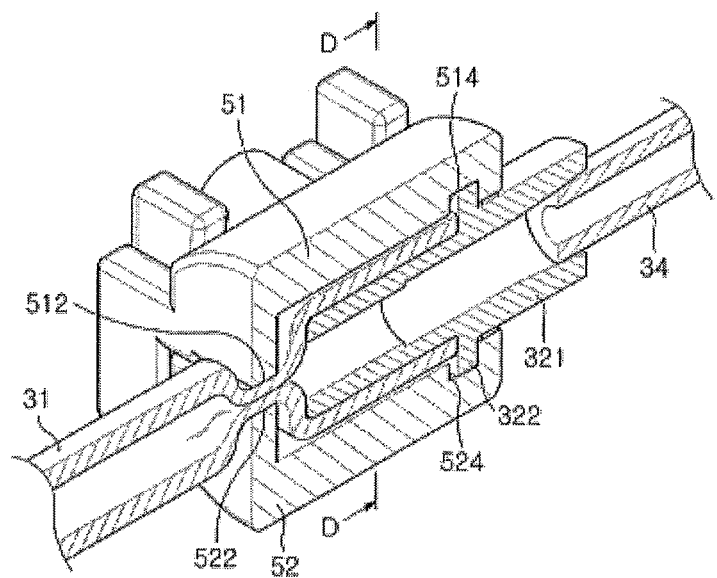
FIG. 10 is a sectional view taken along line C-C of FIG. 8.
Figure 11:
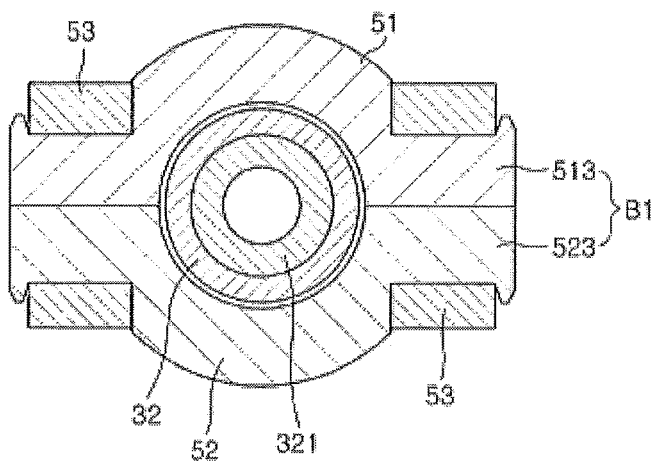
FIG. 11 is a sectional view taken along line D-D of FIG. 10.
Figure 13:
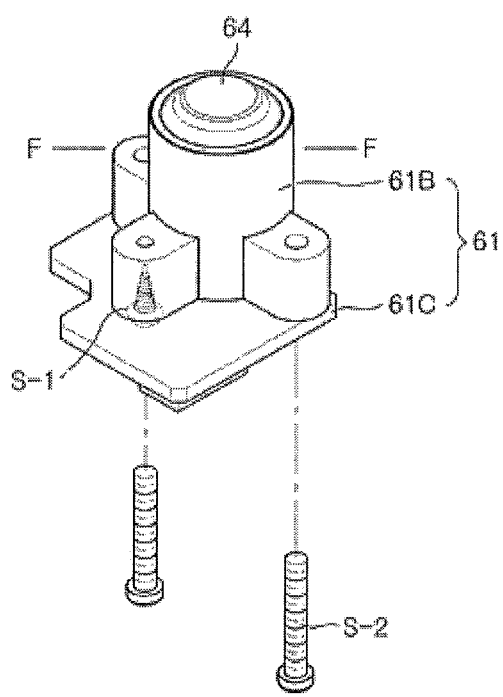
Figure 14:
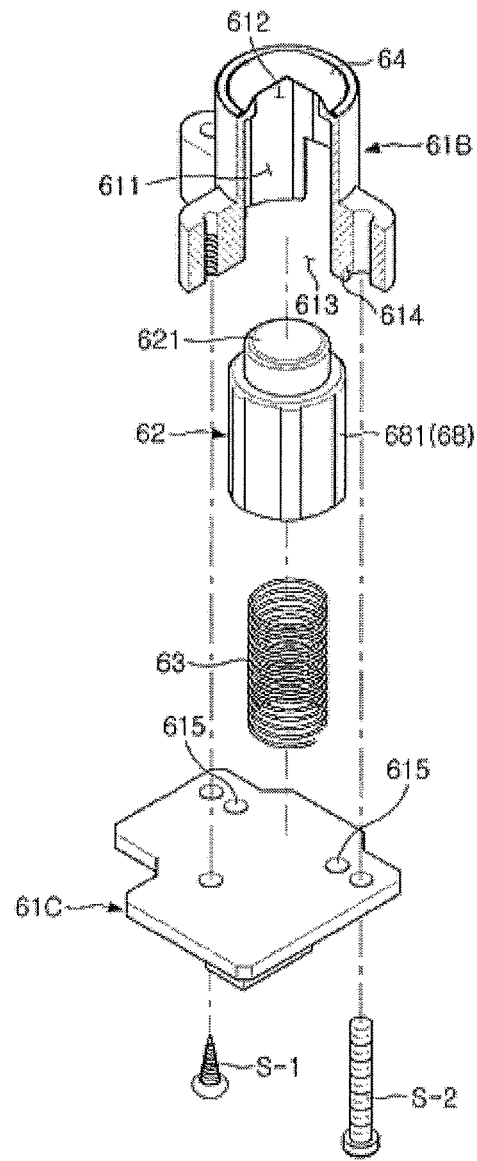
Figure 15:
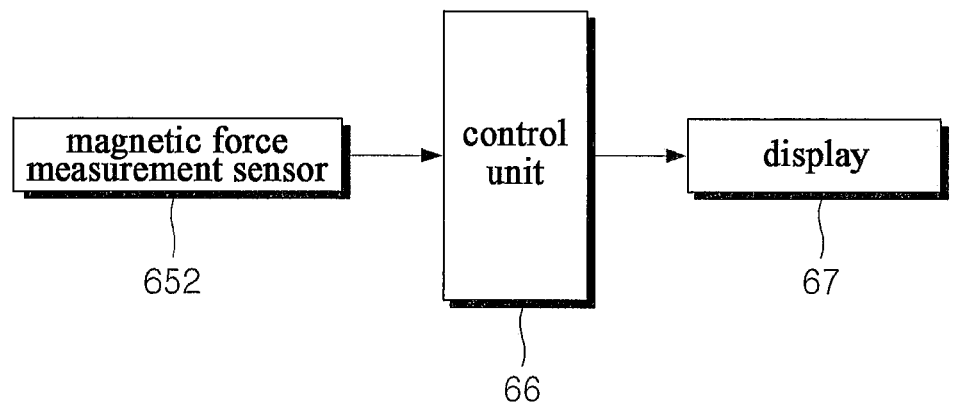
Figure 16:
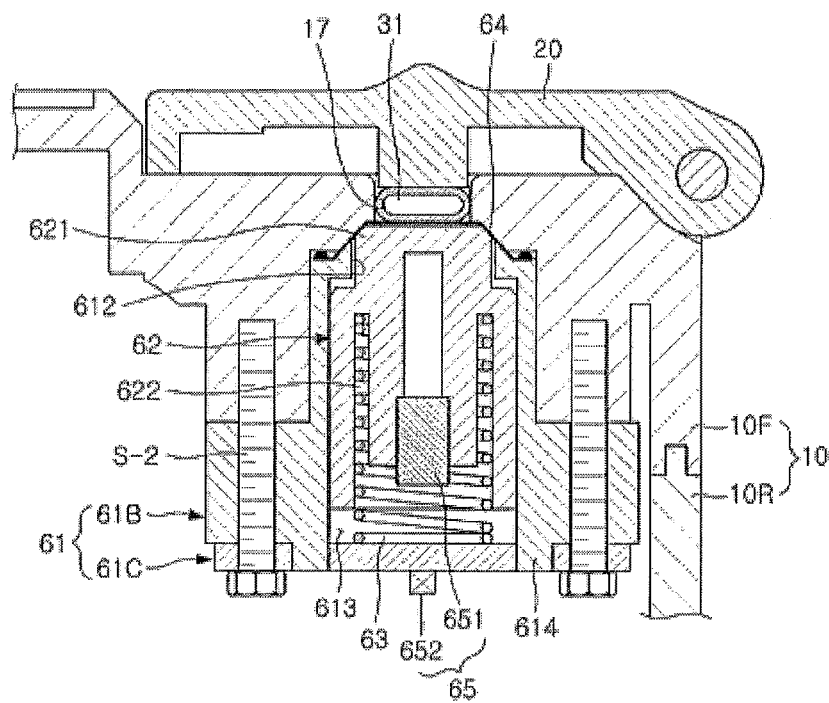
FIGS. 16 and 17 are sectional views taken along line E-E of FIG. 4 to illustrate the installation structure and operation of the tube-blockage detecting device.
Figure 17:
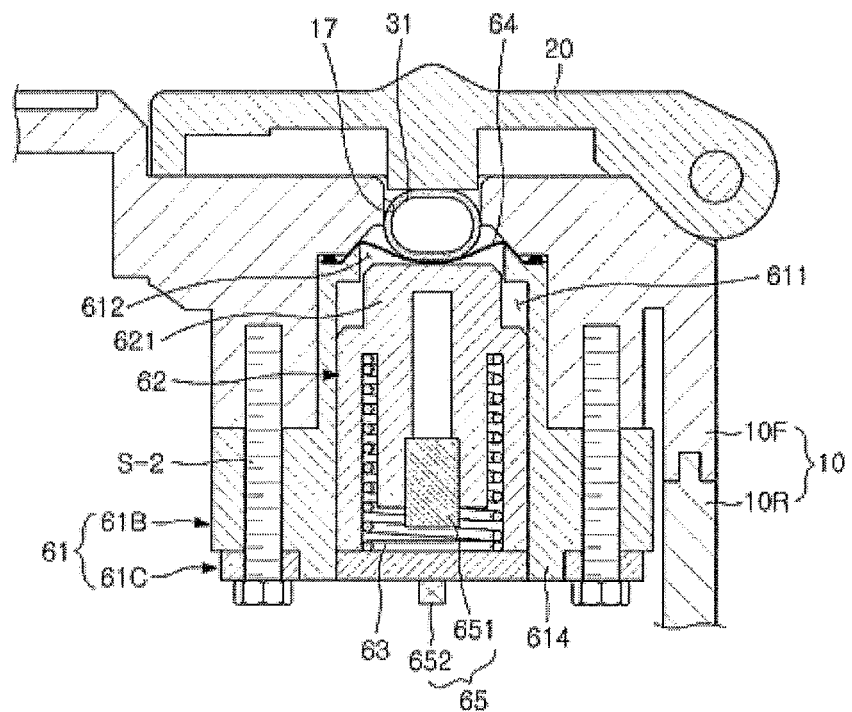
Figure 18:
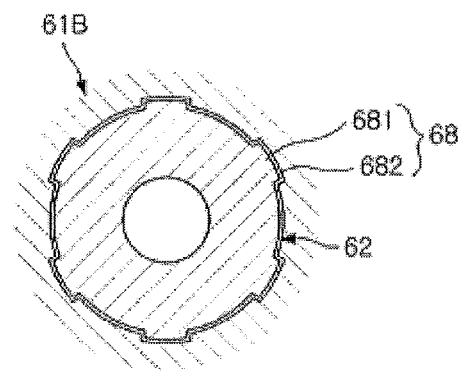
FIG. 18 is a sectional view taken along line F-F of FIG. 13.

FIGS. 5 through 7 illustrate the construction and installation structure of the liquid infusion pump 40. The liquid infusion pump 40 includes a finger module 40M and a cam shaft drive means 40D. The finger module 40M includes a cam shaft 42 which is provided with a spiral cam, and a plurality of fingers 41 which are interlocked with the cam shaft 42 in response to motion conversion operation of the cam shaft 42. The cam shaft drive means 40D rotates the cam shaft 42 so that the fingers 41 move in conjunction with the cam shaft 42 in a wiggling manner.

The fingers 41 are arranged parallel to each other in a row. The cam shaft 42 is rotatably disposed in the fingers 41. The finger module 40M includes a mounting block 43 in which the fingers 41 are installed such that they are interlocked with the cam of the cam shaft 42. The mounting block 43 has a finger receiving space 431. The fingers 41 are disposed in the finger receiving space 431. The mounting block 43 is configured such that one end of each finger 41 can protrude a predetermined length out of the mounting block 43. A perimeter surface of the finger receiving space 431 that encloses the fingers 41 functions as a guide surface which guides individual linear movement of the fingers 41 that are interlocked with the cam of the cam shaft 42. The opposite ends of the cam shaft 41 that is disposed in the fingers 41 are rotatably supported by the mounting block 43. Thereby, when the cam shaft 42 rotates, the operation of the cam makes the fingers 41 individually linearly reciprocate and generally wiggle under guidance of the finger receiving space 431.

The cam shaft drive means 40D includes a stepping motor 44 and a belt-type power transmission unit 45 which transmits rotating power from the stepping motor 44 to the cam shaft 42. The power transmission unit 45 includes two belt pulleys 451 and 452, and a belt 453 which is wound around the belt pulleys 451 and 452. The belt pulleys 451 and 452 are respectively mounted to the cam shaft 42 and the output shaft of the stepping motor 44. Preferably, the belt 453 comprises a timing belt which is made of a material such as rubber which has vibration resistance. Although it is not shown in detail in the drawings, of the two belt pulleys 451 and 452, the drive pulley 451 that is provided on the output shaft of the stepping motor 44 can be fastened to the output shaft of the stepping motor 44 by a vibration resistant coupling which is made of a material such as rubber that has superior vibration resistance.

The stepping motor 44 is disposed such that the output shaft thereof is parallel to the cam shaft 42. The mounting block 43 has a block-shaped shaft support part 432 which rotatably supports the output shaft of the stepping motor 44. The stepping motor 44 is mounted to the shaft support part 432. Here, it is preferable that a coupling member 46 made of rubber or the like that has superior vibration resistance be used in the mounting the stepping motor 44 to the shaft support part 432. That is, the coupling member 46 is interposed between the stepping motor 44 and the shaft support part 432 so that the coupling member 46 can absorb vibrations generated from the stepping motor 44.

As such, the modularized liquid infusion pump 40 is installed in the main body 10 such that the compressing member 25 compresses the portion of the silicon tube 31 that is seated in the tube seating depression 12 and the fingers 41 successively compress the portion of the silicon tube 31 through the finger hole 13. In more detail, the liquid infusion pump 40 is mounted to the front casing 10F by guide pins 47 such that the ends of the fingers 41 that protrude out of the finger receiving space 431 face the finger hole 13 and are able to move forward and backward relative to the finger hole 13. Thus, when each finger 41 moves forward, it come into contact with the silicon tube 31 with the finger hole cover sheet 14 interposed therebetween and thus compresses the silicon tube 31. In addition, the liquid infusion pump 40 is maintained in a state of being biased forward by elastic members 48 that provide elastic force thereto.

In the above-mentioned installation structure of the liquid infusion pump 40, during a liquid infusion process, the fingers 41 can elastically compress the silicon tube 31 without damaging it. In other words, the fingers 41 can be appropriately retracted after moving forward and compressing the silicon tube 31, without excessively compressing the silicon tube 31. Furthermore, because the liquid infusion pump 40 is modularized and mounted to the front casing 10F, the front casing 10F and the rear casing 10R can be easily separated from each other, and the liquid infusion pump 40 can be easily removed from the front casing 10F. Thereby, the assembly of the apparatus can be simplified, and maintenance and repair thereof can be facilitated.

A plurality of through holes 433 that face the finger hole 13 are formed in the mounting block 43 around the finger receiving space 431. The guide pins 47 are inserted into the respective through holes 433 and then threaded into the front casing 10F, thus guiding forward and backward movement of the liquid infusion pump 40 relative to the finger hole 13. For reference, in this embodiment, although four through holes 433 are provided and two are disposed at each of opposite sides of the finger receiving space 431, the number of through holes 433 may be varied.

A coil spring is used as each elastic member 48. Each guide pin 47 has a threaded portion which can be threaded into the front casing 10F on one end thereof. The other end of the guide pin 47 has a head part which serves as a stopper. Each elastic member 48 is provided around the corresponding guide pin 47 in such a way that one end of the elastic member 48 which is a coil spring is supported on the head part of the guide pin 47, and the other end of the elastic member 48 is supported on a portion of the mounting block 43 that defines the corresponding through hole 433. The restoring force of the elastic members 48 biases the liquid infusion pump 40 forward.

In FIGS. 3, 5, and 7, reference numeral 49 denotes at least one pad-type shock absorber which absorbs shock generated when the liquid infusion pump 40 is moved forward by the elastic members 48 and thus the mounting block 43 or other elements collide with the front casing 10F. Collision of the liquid infusion pump 40 with the front casing 10F is mainly caused when the door 20 opens or the liquid infusion tube 30 is removed. In the drawings, although the shock absorber 49 is illustrated as being attached to the front casing 10F, the shock absorber 49 may be attached to the mounting block 43 of the liquid infusion pump 40.

In FIGS. 2 and 4, reference numeral 50 denotes a tube clamp which closes the silicon tube 31 to stop the flow of medical liquid when the door 20 opens, and releases the silicon tube 31 when the door 20 is closed. FIGS. 8 through 12 illustrate the tube clamp 50. Hereinafter, the tube clamp 50 will be explained with reference to FIGS. 8 through 12.

Of the opposite ends of the silicon tube 31, one end, through which medical liquid supplied from the medical liquid storage means is discharged, is connected to a tube connector 32. The tube connector 32 includes a linear cylindrical member 321 the opposite ends of which are respectively connected to the silicon tube 31 and the PVC tube 34. The tube clamp 50 is provided on the junction between the cylindrical member 321 and the silicon tube 31.

The tube clamp 50 includes first and second clamp bodies 51 and 52 which are disposed to face each other with the silicon tube 31 interposed therebetween, and an elastic member 53 which provides elastic force to the first and second clamp bodies 51 and 52 so that they can move towards each other and thus compress and block the silicon tube 31. Under normal conditions, the first and second clamp bodies 51 and 52 are biased to each other by the operation of the elastic member 53, and the silicon tube 31 is maintained in a state of being compressed by the first and second clamp bodies 51 and 52. Of course, if the first and second clamp bodies 51 and 52 move away from each other, the silicon tube 31 is released from the two clamp bodies 51 and 52 that have compressed the silicon tube 31.

The two clamp bodies 51 and 52 of the tube clamp 50 make a pair and enclose the junction between the silicon tube 31 and the cylindrical member 321. Compression parts 512 and 522 which compress the silicon tube 31 are respectively provided on portions of the two clamp bodies 51 and 52 that enclose the silicon tube 31.

Protrusions 513 and 523 are provided on opposite sides of the respective clamp bodies 51 and 52. The protrusions 513 of the first clamp body 51 face the protrusions 523 of the second clamp body 52. The protrusions 513 and 523 make pairs and function as band holders B1. That is, the tube clamp 50 has the two band holders B1 which are formed by the protrusions 513 and 523. A clamp band is fitted over each of the two band holders B1. The clamp band forms the elastic member 53. The clamp band has a loop shape and is made of silicon that has superior restoring force. The clamp bands not only provide elastic force to the two clamp bodies 51 and 52 so that they are biased to each other, but also function to couple the two clamp bodies 51 and 52 to each other.

With the exception of portions of ends of the protrusions 513 and 523 that face each other, a stop protrusion is provided around a portion of the end of each of the protrusions 513 and 523 that make pairs and form the band holders B1. Hence, each band holder B1 has an expanded width on an end thereof. The expanded end of the band holder B1 prevents the clamp band fitted over the band holder B1 from being removed therefrom.

Guide depressions 514 and 524 are respectively formed in the inner surfaces of the two clamp bodies 51 and 52 that face each other. A guide flange 322 is provided around a circumferential outer surface of the cylindrical member 321 and is inserted into the guide depressions 514 and 524 to guide the two clamp bodies 51 and 52 that are moving toward or away from each other. Also, the guide flange 322 and the guide depressions 514 and 524 function as a positioning means for preventing the two clamp bodies 51 and 52 from being displaced from their correct positions.

At least one of legs 515A, 515B, 525A, and 525B is provided on each of the opposite sides of the two clamp bodies 51 and 52. The legs 515A and 515B of the first clamp body 51 protrude towards the second clamp body 52, and the legs 525A and 525B of the second clamp body 52 protrude towards the first clamp body 51. Furthermore, the leg 515A of the first clamp body 51 and the leg 525A of the second clamp body 52 that are disposed at one side of the opposite sides of the clamp bodies 51 and 52 make a pair and contact each other. The leg 515B of the first clamp body 51 and the leg 525B of the second clamp body 52 that are disposed at the other side of the opposite sides of the clamp bodies 51 and 52 also make a pair and contact each other, thus guiding the movement of the clamp bodies 51 and 52 that move toward or away from each other. Further, the legs 515A and 525A that make a pair at one side of the clamp bodies 51 and 52, and the legs 515B and 525B that make a pair at the other side of the clamp bodies 51 and 52, are arranged such that they alternate with each other. Thereby, the two clamp bodies 51 and 52 can be prevented from moving perpendicular to the direction in which they move toward or away from each other, in other words, from wobbling. For reference, in this embodiment, two legs 515A, 515B, 525A, 525B are provided on each of the opposite sides of each clamp bodies 51 and 52. In addition, one band holder B1 is disposed between the legs 515A and 525A that are at one side of the clamp bodies 51 and 52, and the other band holder B1 is disposed between the legs 515B and 525B that are at the other side of the clamp bodies 51 and 52. Preferably, the legs 515A, 515B, 525A, and 525B that make pairs are configured such that their contact surfaces are planar.

A clamp depression 15 which communicates with the tube seating depression 12 is formed in the covered surface at a right side based on the finger hole 13. The tube clamp 50 that is provided on the junction between the silicon tube 31 and the cylindrical member 321 is disposed in the clamp depression 15. Here, the tube clamp 50 is received in the clamp depression 15 such that the silicon tube 31 is disposed between the clamp depression 15 and the first clamp body 51.

With regard to the tube clamp 50 that is disposed in the clamp depression 15, the ends of the legs 515A and 515B of the first clamp body 51 come into contact with the perimeter of the bottom of the clamp depression 15. When the door 20 is closed, the ends of the legs 525A and 525B of the second clamp body 52 make contact with the door 20 so that power of closing the door 20 pushes the second clamp body 52 away from the first clamp body 51. A contact protrusion 21 is provided in the door 20 and is brought into contact with the legs 525A and 525B when the door 20 is closed.

A space-forming depression 16 is formed in a central portion of the bottom of the clamp depression 15 to define a space in which the second clamp body 52 can move away from the first clamp body 51 when the door 20 is closed.

To assemble the tube clamp 50 having the above-mentioned construction, the two clamp bodies 51 and 52 enclose the junction between the silicon tube 31 and the cylindrical member 321 such that the guide flange 322 is inserted into the guide depressions 514 and 524, and then the clamp bands are fitted over the band holders B1 so that the clamp bodies 51 and 52 are coupled to each other. The two clamp bodies 51 and 52 are disposed close to each other by the clamp bands. The silicon tube 31 is compressed and blocked by the compression part 512 and 522. Furthermore, the combination of the guide flange 322 and the guide depressions 514 and 524, and the legs 515B and 525B that alternate with each other and come into contact with each other can prevent the two clamp bodies 51 and 52 from being displaced from their correct positions or wobbling.

Subsequently, the silicon tube 31 is seated into the tube seating depression 12. The tube clamp 50 is received in the clamp depression 15 in such a way that the ends of the legs 515A and 515B of the first clamp body 51 come into contact with the perimeter of the bottom of the clamp depression 15, while the second clamp body 52 is disposed in the space-forming depression 16 (refer to (A) of FIG. 12). Thereafter, the door 20 is closed, thus completing the installation of the liquid infusion tube 30 and the tube clamp 50. Here, when the door 20 is closed, the contact protrusion 21 comes into contact with the legs 522A and 525B of the second clamp body 52, and the power of closing the door 20 overcomes the elastic force of the clamp bands and pushes the second clamp body 52. Thereby, the second clamp body 52 moves away from the first clamp body 51 and into the space forming depression 16. As the second clamp body 52 moves away from the first clamp body 51, the silicon tube 31 that have been compressed by the compression parts 512 and 522 opens and allows liquid infusion (refer to (B) of FIG. 12). Here, the clamp bodies 51 and 52 can be smoothly and reliably moved away from each other under guidance of the guide flange 322, the guide depressions 514 and 524, and the legs 515A and 525A that are put into contact with each other.

Meanwhile, when the door 20 opens, the door 20 releases the clamp bodies 51 and 52 that have been spaced part from each other so that they are moved toward each other by the restoring force of the clamp bands, thus compressing the silicon tube 31 and blocking it.

In FIGS. 3 and 4, reference numeral 60 denotes a tube-blockage detecting device. The tube-blockage detecting device 60 detects whether the liquid infusion tube 30 is blocked by an event in which the outlet-side PVC tube 34 that is connected to the outlet side end of the silicon tube 31 to transfer medical liquid that is supplied from the liquid infusion pump 40 and discharged from the silicon tube 31 is bent or the medical liquid injection unit connected to the outlet-side PVC tube 34 is filled with medical liquid. FIGS. 13 through 18 illustrate the tube-blockage detecting device 60. Hereinafter, the tube-blockage detecting device 60 will be described with reference to FIGS. 13 through 18.

The tube-blockage detecting device 60 includes a mounting housing 61 and a movable member 62. The mounting housing 61 includes a housing body 61B and a housing cover 61C.

The housing body 61B has a receiving space 611 therein in which the movable member 62 is slidably disposed. A through hole 612 and an opening 613 are respectively formed in portions of the housing body 61B that correspond to the opposite ends of the movable member 62 in the direction in which the movable member 62 moves in the receiving space 611. The through hole 612 is smaller than the receiving space 611. The movable member 62 is inserted into or removed from the housing body 61B through the opening 613. The movable member 62 can move toward the through hole 612 or the opening 613 of the housing body 61B. A protruding part 621 is provided on the end of the movable member 62 that faces the through hole 612 of the housing body 61B. When the movable member 62 moves to the through hole 612, the protruding part 621 protrudes out of the housing body 61B through the through hole 612.

The housing cover 61C closes the opening 613 of the housing body 61B. At least one coupling protrusion 614 is provided on a portion of the housing body 61B that is brought into contact with the housing cover 61C. The housing cover 61C has a coupling hole 615 into which the coupling protrusion 614 is inserted. The housing body 61*b* and the housing cover 61C which are coupled to each other by inserting the coupling protrusion 614 into the coupling hole 615 can be reliably fastened to each other by a fastening means S-1 such as a bolt. For reference, the housing cover 61C is a PCB (printed circuit board).

A coil spring 63 is interposed between the housing cover 61*c* and the movable member 62. The coil spring 63 applies elastic force to the movable member 62 so that the protruding part 621 of the movable member 62 can protrude out of the housing body 61B through the through hole 612. The movable member 62 has a spring seating depression 622 in which one end of the coil spring 63 is disposed. The other end of the coil spring 63 that is disposed in the spring seating depression 622 is supported on the housing cover 61C.

The housing body 61B is provided with a through hole cover sheet 64 which is made of a soft material and covers the through hole 612 so as to prevent foreign substances from entering the housing body 61B through the through hole 612.

Preferably, the through hole cover sheet 64 has water resistance and functions as a waterproofing sheet in the same manner as the finger hole cover sheet 14.

A control hole 17 is formed in a portion of the bottom of the tube seating depression 12 that is at the right side of the finger hole 13 at which the outlet side of the silicon tube 31 is disposed, in other words, formed between the finger hole 13 and the clamp depression 15. The mounting housing 61 is disposed in the main body 10 and behind the front casing 10F such that the through hole 612 is aligned with the control hole 17. Because the mounting housing 61 is installed as described above, the through hole cover sheet 64 is interposed between the front casing 10F and the mounting housing 61. The through hole cover sheet 64 covers the control hole 17, thus preventing foreign substances from entering the housing body through the control hole 17. The movable member 62 moves forward or backward relative to the control hole 17 that is at the outlet side of the silicon tube 31. When the movable member 62 moves forward, the protruding part 621 approaches the outlet-side portion of the silicon tube 31 through the control hole 17. Preferably, the control hole 17 is smaller than the through hole 612.

The tube-blockage detecting device 60 includes a displacement detecting means 65, a control unit 66, and a display 67. The displacement detecting means 65 detects variation in the position of the movable member 62 that has approached the outlet-side portion of the silicon tube 31 using the operation of the coil spring 63. The control unit 66 determines whether the liquid infusion tube 30 is blocked based on the result of the detection of the displacement detecting means 65. The display 67 functions as a means for indicating whether the liquid infusion tube 30 is blocked or not under the control of the control unit 66.

If the outlet-side PVC tube 34 is bent or the medical liquid injection unit is filled with medical liquid so that the liquid infusion tube 30 is blocked, the outlet-side portion of the silicon tube 31 is expanded by medical liquid which is being continuously supplied by the liquid infusion pump 40 but cannot flow. At this time, the outlet-side portion of the silicon tube 31 that is being expanded pushes the movable member 62 backward (refer to FIG. 17). The displacement detecting means 65 detects variation in the position of the movable member 62 that moves backward.

The displacement detecting means 65 includes a magnet 651 and a magnetic force measurement sensor 652. The magnet 651 is mounted to the movable member 62 and disposed in the coil spring 63. The magnet 651 moves along with the movable member 62. The magnetic force measurement sensor 652 is provided on the housing cover 61C such that it is spaced apart from the magnet 651 by a predetermined distance in the direction in which the movable member 62 moves. The magnetic force measurement sensor 652 measures magnetic force of the magnet 651. In this embodiment, a hole sensor is used as the magnetic force measurement sensor 652.

The control unit 66 compares a measured value input from the magnetic force measurement sensor 652 with a preset value. If the measured value is greater than the preset value, the control unit 66 determines that the liquid infusion tube 30 has been blocked by a cause such as the outlet-side PVC tube 34 being bent or the medical liquid injection unit is filled with medical liquid. Then, the control unit 66 outputs a control signal and operates the display 67 to notify that the liquid infusion tube 30 has been blocked. When it is determined that the liquid infusion tube 30 has been blocked, the control unit 66 operates the display 67 and simultaneously may control the operation of the stepping motor 44 to stop the liquid infusion pump 40. For reference, in this embodiment, the preset value may be a magnet force value of the magnet 651 when the movable member 62 is adjacent to the outlet-side portion of the silicon tube 31.

In the drawings, reference numeral 68 denotes guides which guide the movable member 62 so that it can precisely move. Each guide 68 includes a guide protrusion 681 and a guide depression 682 which make a pair. The guide protrusion 681 is provided around a circumferential outer surface of the movable member 62. The guide depression 682 is formed in a sidewall of the receiving space 611. Of course, the locations of the guide protrusion 681 and the guide depression 682 may be switched with each other. The guide depression 682 extends long in the direction in which the movable member 62 moves. In the drawings, reference character S-2 denotes a coupling means which is used to install the mounting housing 61.

In an embodiment, some of guides 68 may not include either the guide protrusion 681 or the guide depression 682. In this case, the guide protrusion 681 or the guide depression 682 which does not make a pair functions as a friction-reducing protrusion or depression which reduces friction between the movable member 62 and the receiving space 611 and enhances the mobility of the movable member 62.

Although the preferred embodiment of the present invention has been disclosed for illustrative purposes, those skilled in the art will appreciate that various modifications, additions, and substitutions are possible, without departing from the scope and spirit of the invention as disclosed in the accompanying claims.

The invention claimed is:

1. A liquid infusion apparatus, comprising:
a main body having an opening;
a door installed on the main body so as to be openable, wherein when the door is closed, the door faces the opening with a liquid infusion tube interposed between the door and the opening and supports the liquid infusion tube;
a finger module comprising a plurality of fingers installed in the main body so as to be movable forward and backward relative to the opening, the fingers moving in conjunction with a cam shaft in a wiggling manner in which the fingers successively move forward to the opening and compress a portion of the liquid infusion tube through the opening;
an elastic member applying elastic force to the finger module and biasing the finger module forward so that the liquid infusion tube is elastically compressed by the fingers; and
cam shaft drive means rotating the cam shaft so that the fingers move in conjunction with the cam shaft in the wiggling manner,
wherein the finger module comprises a mounting block provided such that the fingers are able to move in conjunction with the cam shaft in the wiggling manner and compress the liquid infusion tube,
wherein the mounting block is mounted to the main body in such a way that the mounting block is able to move forward and backward relative to the opening under guidance of a guide, and
the cam shaft drive means comprises a motor and a power transmission unit transmitting rotational force of the motor to the cam shaft,
wherein the motor is installed in the mounting block, and the cam shaft drive means moves along with the finger module forward and backward relative to the opening,
wherein the main body comprises a front casing having the opening; and a rear casing coupled to the front casing,
the guide comprises a plurality of guide pins coupled to the front casing and disposed in predetermined portions of the mounting block, and
the elastic member comprises a plurality of elastic members provided around the respective guide pins to bias the mounting block forward.

2. The liquid infusion apparatus according to claim 1, wherein
the mounting block has a shaft support part supporting an output shaft of the motor, and
the motor is coupled to the shaft support part by a coupling member made of an anti-vibration material.

3. The liquid infusion apparatus according to claim 1, wherein a shock absorber is provided on at least one of portions of the main body and the finger module that face each other.

4. The liquid infusion apparatus according to claim 1, further comprising
a cover sheet covering the opening to prevent a foreign substance from entering the main body through the opening, the cover sheet being made of a soft material.

\* \* \* \* \*